United States Patent
Zhao (10) Patent No.: US 10,424,078 B2
(45) Date of Patent: Sep. 24, 2019

(54) HEIGHT MEASURING SYSTEM AND METHOD (71) Applicant: BOE TECHNOLOGY GROUP CO., LTD., Beijing (CN)

(72) Inventor: Xingxing Zhao, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 59 days.

(21) Appl. No.: 15/527,706

(22) PCT Filed: Jun. 8, 2016

(86) PCT No.: PCT/CN2016/085254
§ 371 (c)(1),
(2) Date: May 17, 2017

(87) PCT Pub. No.: WO2017/156894
PCT Pub. Date: Sep. 21, 2017

(65) Prior Publication Data
US 2018/0108143 A1    Apr. 19, 2018

(30) Foreign Application Priority Data
Mar. 18, 2016 (CN) .......................... 2016 1 0158363

(51) Int. Cl.
G06T 7/70 (2017.01)
G01B 11/06 (2006.01)
(Continued)

(52) U.S. Cl.
CPC ............. G06T 7/70 (2017.01); A61B 5/0077 (2013.01); A61B 5/1072 (2013.01);
(Continued)

(58) Field of Classification Search
CPC ............. G06T 7/70; G06T 2207/10028; G06T 2207/30196; A61B 5/1079; A61B 5/1072;
(Continued)

(56) References Cited

U.S. PATENT DOCUMENTS

| | | | |
|---|---|---|---|
| 9,336,607 B1 * | 5/2016 | Chang | G06T 7/73 |
| 2013/0182904 A1 * | 7/2013 | Zhang | H04N 7/18 382/103 |
| 2014/0348417 A1 | 11/2014 | Moore et al. | |

FOREIGN PATENT DOCUMENTS

| | | |
|---|---|---|
| CN | 102090894 A | 6/2011 |
| CN | 102657532 A | 9/2012 |

(Continued)

OTHER PUBLICATIONS

First Chinese Office Action, for Chinese Patent Application No. 201610158363.7, dated Oct. 27, 2017, 8 pages.
(Continued)

Primary Examiner — Amandeep Saini
(74) Attorney, Agent, or Firm — Kinney & Lange, P.A.

(57) ABSTRACT

Disclosed is a height measuring system and method. The height measuring system of the disclosure comprises an image obtaining unit configured to obtaining a depth image and a processing unit configured to analyze and determine a ground and a top of a head of a human body in the depth image and calculating a distance between the top of the head of the human body and a plane of the ground as a height.

12 Claims, 5 Drawing Sheets (51) Int. Cl.

| | |
|---|---|
| *G01B 11/22* | (2006.01) |
| *G01B 11/24* | (2006.01) |
| *A61B 5/00* | (2006.01) |
| *A61B 5/107* | (2006.01) |
| *G06T 7/60* | (2017.01) |
| *G06T 7/73* | (2017.01) |

(52) U.S. Cl.
CPC ........ *A61B 5/1079* (2013.01); *G01B 11/0608* (2013.01); *G01B 11/22* (2013.01); *G01B 11/24* (2013.01); *G06T 7/60* (2013.01); *G06T 7/75* (2017.01); *A61B 2562/0219* (2013.01); *G06T 2207/10012* (2013.01); *G06T 2207/10024* (2013.01); *G06T 2207/10028* (2013.01); *G06T 2207/30196* (2013.01)

(58) Field of Classification Search
CPC .......... A61B 5/0077; A61B 2562/0219; G01B 11/0608; G01B 11/24; G01B 11/22

USPC ....................................................... 382/106
See application file for complete search history.

(56) References Cited

FOREIGN PATENT DOCUMENTS

| | | | |
|---|---|---|---|
| CN | 103389042 A | 11/2013 | |
| CN | 103499334 A | 1/2014 | |
| CN | 104173054 A | 12/2014 | |
| KR | 101608889 B1 * | 4/2016 | ........... G06K 9/6202 |

OTHER PUBLICATIONS

English Translation of International Search Report and Written Opinion for PCT Patent Application No. PCT/CN2016/085254, dated Nov. 28, 2016, 11 pages.

* cited by examiner

HEIGHT MEASURING SYSTEM AND METHOD

CROSS-REFERENCE TO RELATED APPLICATION

This application is a national phase application from PCT/CN2016/085254 filed on Jun. 8, 2016 and claims the benefit of Chinese Patent Application No. CN201610158363.7 filed on Mar. 18, 2016 in the State Intellectual Property Office of China, the whole disclosure of which is incorporated herein by reference.

BACKGROUND OF THE INVENTION

Field of the Invention

Embodiments of the disclosure relate to field of height measuring technique, in particular to a height measuring system and method.

Description of the Related Art

A conventional height measuring method is carried out by a meter and the like. Thus, this measurement needs cooperation of a human body and can not be carried out in real time.

In the prior art, a technique for determining a height through capturing and analyzing an image of the human body is proposed. This measurement does not need the cooperation of the human body, as long as the human body is located in a range of the image capturing. Further, this measurement can be made in real time.

For example, an existing height measuring method comprises determining feet and a top of a head of the human body through analysis and determining a distance therebetween as the height. However, such method has disadvantageous in which it is difficult to determine the position of the feet of the human body since the feet is prone to be adhered to a ground, which may affect accuracy of the measurement. Further, since the feet are located at a relative low position, they may be easily shaded by a table, a chair or the like so as not to be visible. Thus, this method in this case is disable.

Figure 1:
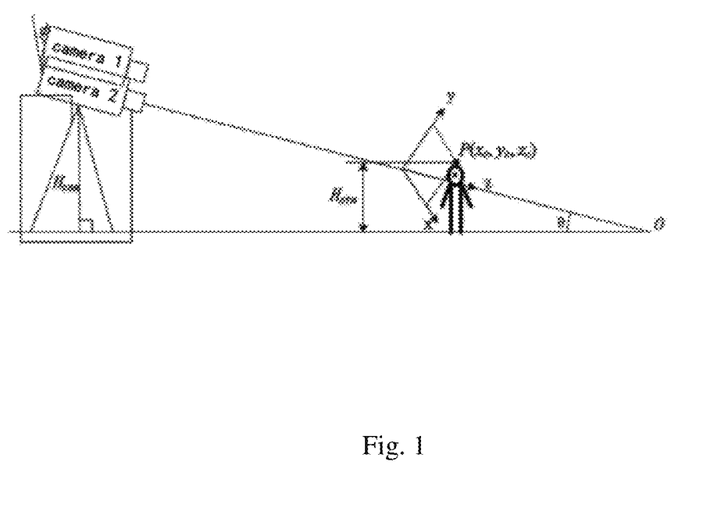
FIG. 1 is a schematic view of a height measuring method in the prior art.

In another example, as shown in FIG. 1, another existing height measuring method comprises capturing an image of the human body by two-eyes camera and calculating a height according to a height difference between a top of a head of the human body and the camera. However, in this method, it is necessary to predetermine a placing height, position, angle and the like of the camera. Once the placing height, position and angle of the camera are determined, it can not move, which may result in inconvenient utilization.

SUMMARY OF THE INVENTION

The disclosure is intended to provide a height measuring system and method which at least solves one of the defects in the prior art.

According to one aspect of the disclosure, there is provided a height measuring system comprising: an image obtaining unit configured to obtaining a depth image; and a processing unit configured to analyze and determine a ground and a top of a head of a human body in the depth image and calculating a distance between the top of the head of the human body and a plane of the ground as a height.

Optionally, the image obtaining unit comprises an image capturing unit.

Further optionally, analyze and determine a ground in the depth image comprises: obtaining all planar surfaces in the depth image through analysis; and determining a maximum planar surface located at a lower part of the depth image and away from the image capturing unit by a distance less than a predetermined value as the ground.

Further optionally, the predetermined value is 3 m.

Further optionally, the height measuring system further comprises a gravity sensor provided on the image capturing unit for sensing a gravity direction; analyze and determine a ground in the depth image comprises: obtaining all planar surfaces in the depth image through analysis; and determining a planar surface perpendicular to the gravity direction and located at a lowest position in the gravity direction as the ground.

Optionally, analyze and determine a top of a head of a human body in the depth image comprises: identifying the human body in the depth image through a human body segmentation technique; and determining a point in an integrate portion of the human body farthest away from the plane of the ground as the top of the head of the human body.

Optionally, analyze and determine a ground and a top of a head of a human body in the depth image comprises: analyzing and determining the top of the head of the human body from a depth image of a current frame; and analyzing and determining the ground from one or more depth images of one or more previous frames before the current frame if the ground can not be determined from a depth image of the current frame.

Optionally, the processing unit is further configured to establish a coordinate system and determine a coordinate of each pixel in the depth image; analyze and determine a ground and a top of a head of a human body in the depth image comprises: analyzing and determining a plane equation $Ax+By+Cz+D=0$ of the plane of the ground, wherein x, y, z are coordinate values of a pixel point (x, y, z) on the plane; and determining coordinate values $x_0$, $y_0$, $z_0$ of a coordinate point $(x_0, y_0, z_0)$ of the top of the head of the human body through analysis.

Further optionally, calculating a distance between the top of the head of the human body and a plane of the ground as a height comprises: calculating the distance High as the height according to the following formula:

$$\text{High} = \frac{A*x_0 + B*y_0 + C*z_0 + D}{\sqrt{A^2 + B^2 + C^2}}.$$

According to another aspect of the disclosure, there is provided a height measuring method comprising:
obtaining a depth image;
analyzing and determining a ground in the depth image;
analyzing and determining a top of a head of a human body in the depth image;
calculating a distance between the top of the head of the human body and a plane of the ground as the height.

Optionally, the depth image is obtained by an image capturing unit.

Optionally, analyze and determine a ground in the depth image comprises:
obtaining all planar surfaces in the depth image through analysis; and determining a maximum planar surface located at a lower part of the depth image and away from the image capturing unit by a distance less than a predetermined value as the ground.

Optionally, the predetermined value is 3 m.

Optionally, the height measuring method further comprising:

sensing a gravity direction by a gravity sensor, and wherein analyze and determine a ground in the depth image comprises:

a. obtaining all planar surfaces in the depth image through analysis; and b. determining a planar surface perpendicular to the gravity direction and located at a lowest position in the gravity direction as the ground.

Optionally, analyze and determine a top of a head of a human body in the depth image comprises:

identifying the human body in the depth image through a human body segmentation technique; and determining a point in an integrate portion of the human body farthest away from the plane of the ground as the top of the head of the human body.

Optionally, analyze and determine a ground in the depth image comprises:

analyzing and determining the ground from one or more depth images of one or more previous frames before the current frame if the ground can not be determined from a depth image of the current frame.

Optionally, calculating a distance between the top of the head of the human body and a plane of the ground as a height comprises:

establishing a coordinate system and determining a coordinate of each pixel in the depth image;

determining a plane equation $Ax+By+Cz+D=0$ of the plane of the ground through fitting, wherein x, y, z are coordinate values of a pixel point (x, y, z) on the plane; and determining coordinate values $x_0$, $y_0$, $z_0$ of a coordinate point ($x_0$, $y_0$, $z_0$) of the top of the head of the human body; and calculating the distance High as the height according to a formula as below $$High = \frac{A*x_0 + B*y_0 + C*z_0 + D}{\sqrt{A^2 + B^2 + C^2}}.$$

An embodiment of the present invention provides a height measuring method comprising:

obtaining a depth image;

analyzing whether a ground can be determined through a depth image of a current frame, if it is, proceeding to the next step, if it is not, analyzing a depth image of one or more previous frames before the current frame to determine the ground;

obtaining a ground equation through fitting;

obtaining a human body in the depth image of the current frame through a human body segment technique;

determining a point in an integrate portion of the human body farthest away from a plane of the ground as a top of a head of the human body and obtaining coordinate values of the point, and calculating a distance between the top of the head of the human body and the plane of the ground as a height.

DETAILED DESCRIPTION OF PREFERRED EMBODIMENTS OF THE INVENTION

In order to make those skilled in the art understand the technical scheme of the disclosure better, the disclosure will be described in detail with reference to the accompanying drawings and embodiments.

Figure 2:
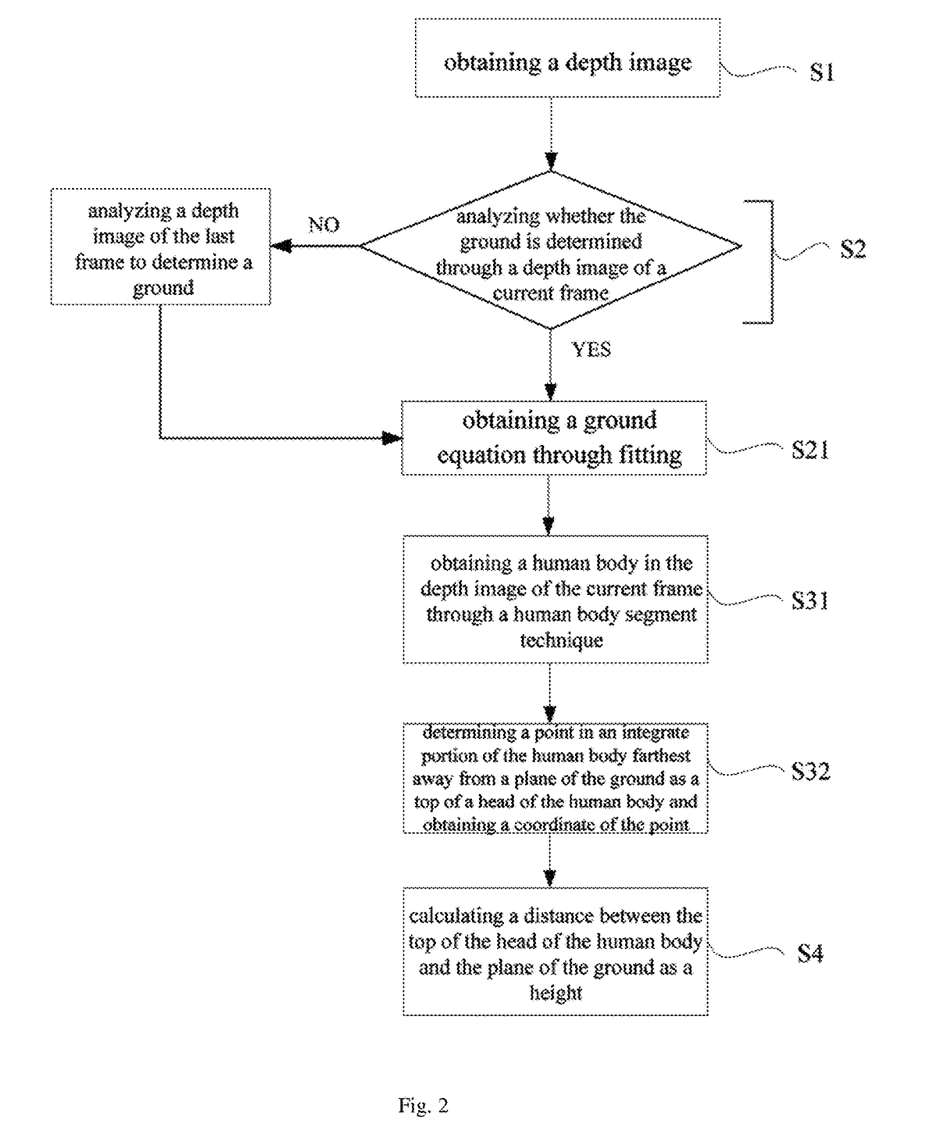
FIG. 2 is a flow chart of a height measuring method according to an exemplary embodiment of the disclosure.
Figure 6:
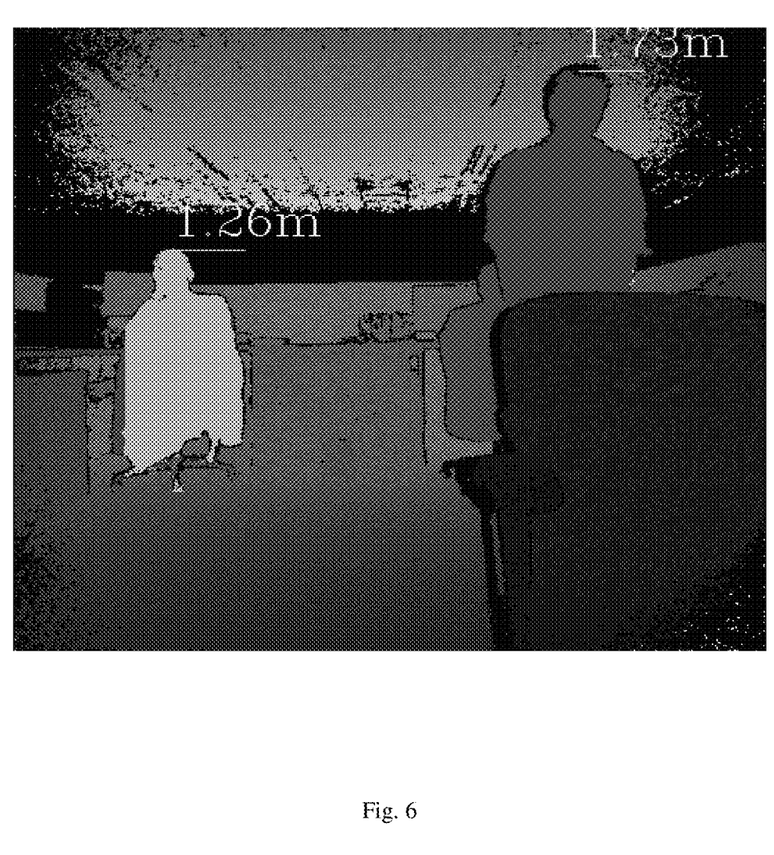
FIG. 6 is a schematic view of another analysis result of a height measuring system according to an exemplary embodiment of the disclosure.

As shown in FIGS. 2 and 6, according to an exemplary embodiment of the disclosure, there is provided a height measuring system comprising:

an image obtaining unit configured to obtain a depth image; and a processing unit configured to analyze and determine a ground and a top of a head of a human body in the depth image obtained by the image obtaining unit and calculate a distance between the top of the head of the human body and a plane of the ground as a height.

Figure 3:
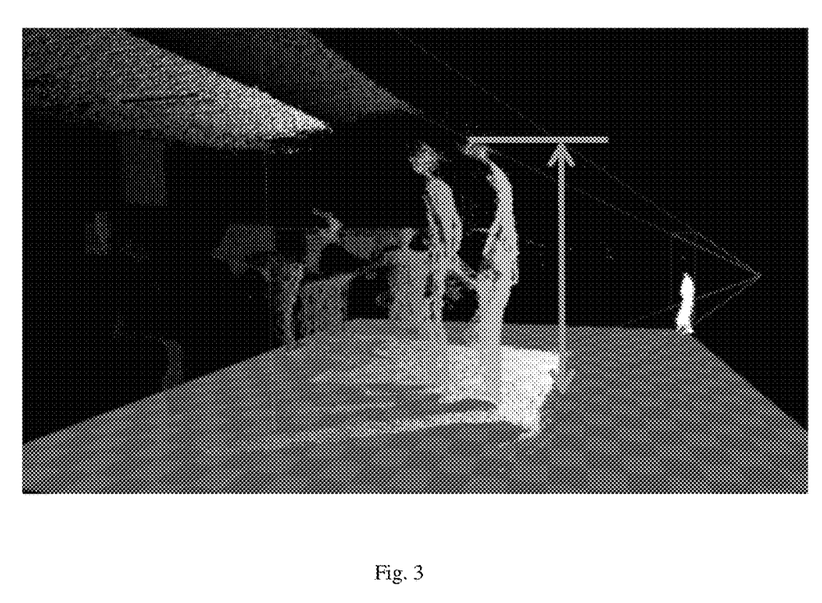
FIG. 3 is a depth image obtained by a height measuring system according to an exemplary embodiment of the disclosure.

That is, the height measuring system according to the embodiment of the disclosure comprises the image obtaining unit for obtaining the depth image of the human body to be measured and the ground. The depth image is a stereo image in which color information of each pixel is recorded and a distance and relative angle between each pixel and the image obtaining unit are also recorded, thereby a relative spatial position of each pixel may be determined. Thereafter, the processing unit may determine pixels of the human body in the depth image, i.e., pixels in the depth image forming an image of the human body, and pixels of the ground, i.e., pixels in the depth image forming an image of the ground, through analysis. After determining the pixels of the human body, it is possible to determine a position of the top of the head of the human body. Further, since the ground is planar in most cases, it is possible to determine the plane of the ground only through analyzing to obtain a partial ground which is a ground of finite area visible in the depth image, rather than an infinite plane. Then, a distance between the plane of the ground and the top of the head of the human body is calculated. This distance is also a distance between feet to the top of the head of the human body, which is a height. In addition, an example of the depth image is shown in FIG. 3, and the detailed description thereof will be omitted herein.

Figure 5:
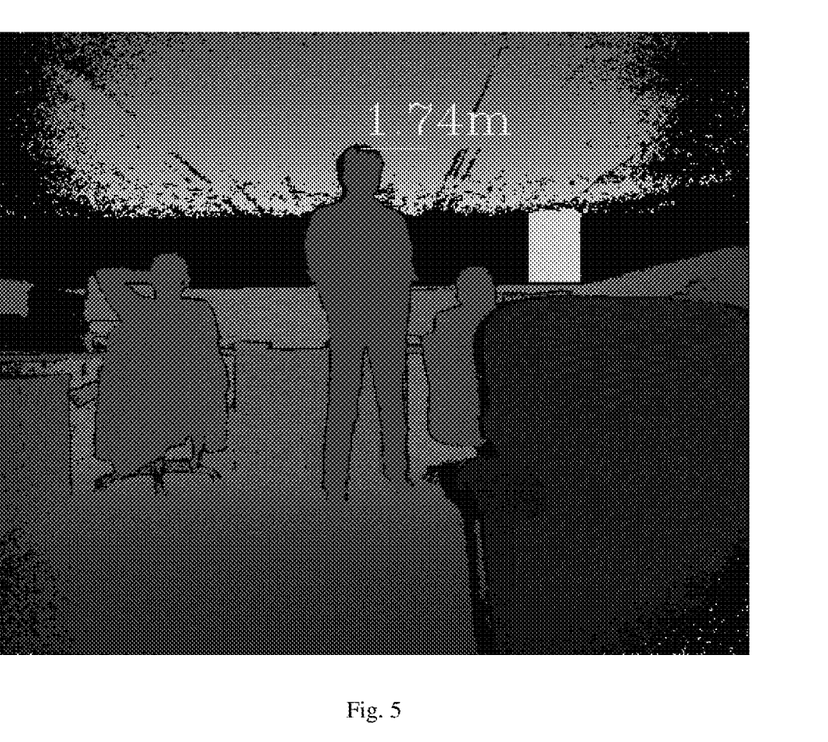
FIG. 5 is a schematic view of an analysis result of a height measuring system according to an exemplary embodiment of the disclosure.

In the height measuring system according to embodiments of the disclosure, the height is determined through determination of the top of the head of the human body and the ground. Thus, there is no step of separating the feet of the human body, which results in higher accuracy. Further, since the plane for measurement is the plane of the ground, the height measuring system is suitable for a case where the feet of the human body is visible, as shown in FIG. 5, and is also suitable for a case where the feet of the human body and the ground under the feet are shaded, as shown in FIG. 6, as long as the top of the head of the human body is not shaded. Meanwhile, since the height measuring system determines the height through the distance between different objects in the depth image, there is no requirement on a placing position, height of a camera, thus has convenient utilization.

In some embodiments of the disclosure, the image obtaining unit is an image capturing unit such as a depth camera.

That is to say, the image obtaining unit may for example include a depth camera for capturing an image in real time, and the image captured by the depth camera is then processed by the processing unit. The depth camera is the existing device for capturing the depth image, and the detailed description thereof is omitted herein.

Of course, the image obtaining unit may also include a computer or a network component for obtaining the depth image captured and stored by other devices and outputting the depth image to the processing unit to be processed.

In some embodiments of the disclosure, determining the ground in the depth image obtained by the image obtaining unit through analysis comprises obtaining all planar surfaces in the depth image through analysis, and determining a maximum planar surface located at a lower part of the depth image and away from the image capturing unit by a distance less than a predetermined value as the ground.

The predetermined value is set as 3 m.

The depth image may only contain a number of pixels. However, the height measuring system does not know which pixels are the pixels of the ground. Thus, it is necessary to determine the ground, i.e., the pixel of the ground, through analysis. In a case where a position of each pixel is known, it is possible to simply determine the pixels located on same plane and abutted with each other through analysis. These pixels are formed as a planar surface. This planar surface is a plane of finite area, rather than a plane of infinite area. Therefore, it is possible to obtain all the planar surfaces in the depth image, including the ground, a surface of a table, a surface of a cabinet and the like through analysis. Generally, the image obtaining unit such as the image capturing unit is placed straight as a whole, thus the ground is generally located at a lower part of the depth image. Further, the ground typically has a larger area and is not too far away from the image capturing unit. Therefore, it is possible to determine the maximum planar surface in all planar surfaces located at the lower part of the depth image and away from the image obtaining unit such as the image capturing unit by the distance less than the predetermined value as the ground. According to experiential analysis, in most cases, the ground may appear in a range of 3 m in the depth image from the image obtaining unit such as the image capturing unit. If the predetermined value is too large, this range may include other planar surfaces such as the surface of the table, which may result in an inaccurate determination. Thus, the above predetermined value is set as 3 m.

In some embodiments of the disclosure, the height measuring system further comprises a gravity sensor provided on the image capturing unit for sensing a gravity direction. Determining the ground in the depth image through analysis comprises obtaining all planar surfaces in the depth image through analysis, and determining a planar surface perpendicular to the gravity direction and located at a lowest position in the gravity direction as the ground.

That is, the image obtaining unit such as the image capturing unit is additionally provided with the gravity sensor for sensing the gravity. Thus, it is possible to determine the gravity direction in the depth image. In other words, it is possible to determine a direction in the depth image corresponding to a lower part in the real word. Obviously, the ground is typically perpendicular to the gravity direction and located at the lowest position in the gravity direction. Thus, it is possible to determine a planar surface perpendicular to the gravity direction and located at the lowest position in the gravity direction as the ground.

Of course, the method for determining the ground through analysis based on the depth image is not limited to the above, and other method for determining the ground is possible.

In some embodiments of the disclosure, determining the top of the head of the human body in the depth image through analysis comprises identifying the human body in the depth image through a human body segmentation technique, and determining a point in a connected region of the human body farthest away from the plane of the ground as the top of the head of the human body.

That is to say, it is possible to identify the human body in the depth image through the human body segmentation technique. Particularly, the human body segmentation technique may be implemented by the existing software such as kinect software of Microsoft. Since the technique for identifying the human body through analysis is known in the art, the detailed description thereof is omitted herein. After identifying the human body, i.e., determining the pixels of the human body, it is possible to determine a pixel in the pixels of the human body farthest away from the plane of the ground and further determine the pixel as the top of the head of the human body. However, the existing human body segmentation technique is mainly used in field of body feeling, articulation analysis and the like, the analyzed human body thus may contain some noises outside the human body, such as noises located above the head top of the human. These noises do not substantially affect the body feeling, articulation analysis. However, if these noises are mistaken as the top of the head of the human body, they would affect the result of the height measurement. Therefore, in embodiments of the disclosure, the point in the integrate portion of the human body, i.e., a main portion of the human body obtained through analysis, farthest away from the plane in which the ground is located is determined as the top of the head of the human body, thereby eliminating the affect of the noises to improve the accuracy of the measurement.

It should be understood in order to determine the ground through analysis, the ground in the depth image should be visible and sufficiently large. However, in some cases, most part of the ground is shaded, for example, in a case where there are many human bodies in the depth image. At this time, it is difficult to determine the ground through analyzing the depth image. In this case, since the image obtaining unit is typically not movable, the position of the ground in the depth image of different frames is not changed and only the human bodies move. Thus, it is possible to analyze and determine the ground from the depth image of the previous other frames such as the last frame or the previous several frames, and then to calculate the height through the ground together with the top of the head of the human body in the depth image of this frame, because the height to be measured is obviously the height in the depth image of the current frame.

Thus, in some embodiments of the disclosure, determining the ground and the top of the head of the human body through analysis comprises determining the top of the head of the human body through analyzing from the depth image of the current frame. If the ground can not be determined through analyzing from the depth image of the current frame, the ground may be determined through analyzing from the depth image of the last frame or server frames of the current frame.

Note that, in embodiments of the disclosure, there is no limitation on the sequence for determining the top of the head of the human body and the ground, as long as the top of the head of the human body and the ground are ultimately determined.

In some embodiments of the disclosure, the processing unit is also configured to establish a coordinate system and determine a coordinate of each pixel in the depth image in the coordinate system. Analyzing and determining the ground and the top of the head of the human body in the depth image comprises analyzing and determining a plane equation $Ax+By+Cz+D=0$ of the plane of the ground, and determining the coordinate $(x_0, y_0, z_0)$ of the top of the head of the human body.

In some embodiments of the disclosure, calculating the distance between the top of the head of the human body and the plane of the ground as the height comprises calculating the distance High as the height according to the formula.

Figure 4:
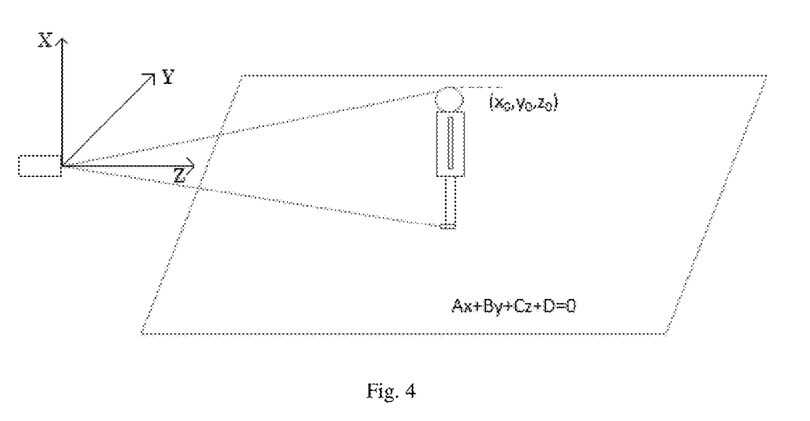
FIG. 4 is a schematic view of analyzing a height by a height measuring system according to an exemplary embodiment of the disclosure.

That is, as shown in FIG. 4, it is possible to establish a three-dimensional coordinate system of (x, y, z). For example, if the image obtaining unit is the image capturing unit, it is possible to establish the coordinate system with the position at which the image obtaining unit is located as an original point. Of course, the coordinate system may be established randomly, and is not necessarily established with the image capturing unit as the original point. Since the relative spatial position of each pixel in the depth image is known, the coordinates of all the pixels in the depth image in the three-dimensional coordinate system are also known.

As discussed above, it is possible to determine which pixel in the depth image refers to the top of the head of the human body by the existing method. Thus, the coordinate of this pixel, i.e, the top of the head of the human body, is also known and expressed by $(x_0, y_0, z_0)$.

Accordingly, the pixels in the depth image referring to the ground are also known. Since the ground is a planar surface, the coordinates of all the pixels thereof necessarily satisfy the same plane equation $Ax+By+Cz+D=0$. Therefore, it is possible to solve parameters A, B, C and D in the above plane equation only through taking the coordinates of any three pixels which are not located on the same line into the plane equation and establishing an equation group to obtain the determined plane equation.

In this way, then, it is possible to calculate the height according the above equation relative to the distance between the point to the plane.

As shown in FIGS. 2 to 6, according to embodiments of the disclosure, there is provided a height measuring method comprising:

S1: obtaining a depth image;
S2: obtaining a ground in the depth image through analysis;
S3: obtaining a top of a head of a human body in the depth image through analysis;
S4: calculating a distance between the top of the head of the human body and a plane of the ground as the height.

In some embodiment of the disclosure, the method further comprises sensing a gravity direction by a gravity sensor. In this case, the step S2 comprises obtaining all planar surfaces in the depth image through analysis, and determining a planar surface perpendicular to the gravity direction and located at a lowest position in the gravity direction as the ground.

In some embodiments of the disclosure, it is possible to establish a coordinate system in the depth image and determine a coordinate of each pixel in the depth image. Thus, the step S2 further comprises step S21 of determine a ground equation of the ground, i.e., determining a plane equation $Ax+By+Cz+D=0$ of the plane of the ground, through fitting.

In some embodiments of the disclosure, the step S3 comprises:

S31: identifying the human body in the depth image through a human body segmentation technique; and
S31: determining a point in an integrate portion of the human body farthest away from the plane of the ground as the top of the head of the human body.

It should be understood if the coordinate system is established in the depth image, once the point farthest away from the plane of the ground, i.e., the top of the head of the human body, is determined, the coordinate of this point is known and expressed by $(x_0, y_0, z_0)$.

Therefore, in step S4, it is possible to calculate the distance High as the height according to the formula.

It should be understood in order to determine the ground through analysis, the ground in the depth image should be visible and sufficiently large. However, in some cases, most part of the ground is shaded, for example, in a case where there are many human bodies in the depth image. At this time, it is difficult to determine the ground through analyzing the depth image. In this case, since the image obtaining unit is typically not movable, the position of the ground in the depth image of different frames is not changed and only the human bodies move. Thus, it is possible to analyze the depth image of the previous other frames such as the last frame or the previous several frames to determine the ground, and then to calculate the height through the ground together with the top of the head of the human body in the depth image of this frame, because the height to be measured is obviously the height in the depth image of the current frame.

Thus, the step S2 may comprise determining the ground through analyzing from the depth image of the last frame or server frames of the current frame if the ground can not be determined through analyzing from the depth image of the current frame. As a specific example, as shown in FIG. 2, the height measuring method according to embodiments of the disclosure may comprises:

S1: obtaining a depth image;
S2: analyzing whether a ground is determined through a depth image of a current frame; if it is, proceeding the next step; if it is not, analyzing a depth image of previous frame such as the last frame to determine the ground.
S21: obtaining a ground equation through fitting.
S31: obtaining a human body in the depth image of the current frame through a human body segment technique.
S32: determining a point in an integrate portion of the human body farthest away from a plane of the ground as a top of a head of the human body and obtaining a coordinate of the point.
S4: calculating a distance between the top of the head of the human body and the plane of the ground as a height.

Of course, the sequence of the above steps of obtaining the top of the head of the human body and the plane of the ground is not necessary and may be exchanged with each other or carried out parallel with each other. That is, the steps S2-S21 and the S31-S32 may be exchanged with each other or carried out parallel with each other.

It should be understood that the above embodiments are merely the exemplary implementations for describing the principle of the disclosure, the disclosure, however, is not limited thereto. Various changes and modifications may be made to the disclosure by those skilled in the art without departing from the spirit and scope thereof. These changes and modification fall within the scope of claims.

What is claimed is:

1. A height measuring system comprising;
an image obtaining unit configured to obtain a depth image; and
a processing unit configured to analyze and determine a ground and a top of a head of a human body in the depth image and calculate a distance between the top of the head of the human body and a plane of the ground as a height,
wherein the image obtaining unit comprises an image capturing unit, and
wherein the processing unit is configured to analyze and determine the ground in the depth image by:
obtaining all planar surfaces in the depth image through analysis; and
determining a maximum planar surface which is located at a lower half of the depth image and away from the image obtaining unit by a distance less than a predetermined value as the ground.

2. The height measuring system according to claim 1, wherein the predetermined value is 3 m.

3. The height measuring system according to claim 1, wherein the processing unit is configured to analyze and determine the top of the head of the human body in the depth image by:
identifying the human body in the depth image through a human body segmentation technique; and
determining a point being in an integrate region of the human body and being farthest away from the plane of the ground as the top of the head of the human body.

4. The height measuring system according to claim 1, wherein the processing unit is configured to analyze and determine the ground and the top of the head of the human body in the depth image by:
analyzing and determining the top of the head of the human body from the depth image of a current frame; and
analyzing and determining the ground from one or more depth images of one or more previous frames before the current frame if the ground fails to be determined from a depth image of the current frame.

5. The height measuring system according to claim 1, wherein the processing unit is further configured to establish a coordinate system and determine a coordinate of each pixel in the depth image, and to analyze and determine the ground and the top of the head of the human body in the depth image by:
analyzing and determining a plane equation $Ax+By+Cz+D=0$ of the plane of the ground, wherein x, y, z are coordinate values of a pixel (x, y, z) on the plane; and
analyzing and determining coordinate values $x_0, y_0, z_0$ of a coordinate point $(x_0, y_0, z_0)$ of the top of the head of the human body.

6. The height measuring system according to claim 5, wherein calculating the distance between the top of the head of the human body and the plane of the ground as the height comprises:
calculating the distance High as the height according to a formula:

$$High = \frac{A*x_0 + B*y_0 + C*z_0 + D}{\sqrt{A^2+B^2+C^2}}.$$

7. A height measuring method comprising:
obtaining a depth image;
analyzing and determining a ground in the depth image;
analyzing and determining a top of a head of a human body in the depth image; and
calculating a distance between the top of the head of the human body and a plane of the ground as the height,
wherein the depth image is obtained by an image capturing unit, and
wherein analyzing and determining the ground in the depth image comprises:
obtaining all planar surfaces in the depth image through analysis; and
determining a maximum planar surface which is located at a lower half of the depth image and away from the image capturing unit by a distance less than a predetermined value, as the ground.

8. The height measuring method according to claim 7, wherein the predetermined value is 3 m.

9. The height measuring method according to claim 7, wherein analyzing and determining the top of the head of the human body in the depth image comprises:
identifying the human body in the depth image through a human body segmentation technique; and
determining a point in an integrated portion of the human body farthest away from the plane of the ground as the top of the head of the human body.

10. The height measuring method according to claim 9, wherein calculating the distance between the top of the head of the human body and the plane of the ground as the height comprises:
establishing a coordinate system and determining a coordinate of each pixel in the depth image;
determining a plane equation $Ax+By+Cz+D=0$ of the plane of the ground through fitting, wherein x, y, z are coordinate values of a pixel point (x, y, z) on the plane; and
determining coordinate values x0, y0, z0 of a coordinate point (x0, y0, z0) of the top of the head of the human body; and
calculating the distance High as the height according to a formula as below $$High = \frac{A*x_0 + B*y_0 + C*z_0 + D}{\sqrt{A^2+B^2+C^2}}.$$

11. The height measuring method according to claim 7, wherein analyzing and determining the ground in the depth image comprises:
analyzing and determining the ground from one or more depth images of one or more previous frames before the current frame if the ground fails to be determined from a depth image of the current frame.

12. A height measuring system comprising
an image obtaining unit configured to obtain a depth image; and
a processing unit configured to analyze and determine a ground and a top of a head of a human body in the depth image and calculate a distance between the top of the head of the human body and a plane of the ground as a height,
wherein the image obtaining unit comprises an image capturing unit, wherein the height measuring system further comprises a gravity sensor provided on the image capturing unit for sensing a gravity direction, and wherein the processing unit is configured to analyze and determine the ground in the depth image by:
  obtaining all planar surfaces in the depth image through analysis; and
  determining a planar surface perpendicular to the gravity direction and located at a lowest position in the gravity direction as the ground.

* * * * *